United States Patent [19]
Robeson

[11] Patent Number: 4,784,123

[45] Date of Patent: Nov. 15, 1988

[54] ORTHOPEDIC/ORTHOTIC SPLINT MATERIALS

[75] Inventor: Lloyd M. Robeson, Whitehouse Station, N.J.

[73] Assignee: Union Carbide Corporation, Danbury, Conn.

[21] Appl. No.: 815,925

[22] Filed: Jan. 3, 1986

[51] Int. Cl.$^4$ .............................................. A61F 5/04
[52] U.S. Cl. ................................... 128/90; 128/89 R
[58] Field of Search ............. 128/90, 89 R, 155, 156; 525/415, 440

[56] References Cited

U.S. PATENT DOCUMENTS

| | | |
|---|---|---|
| 4,274,983 | 1/1981 | Kent . |
| 4,286,586 | 9/1981 | Potts . |
| 4,316,457 | 2/1982 | Liegeois . |
| 4,483,333 | 11/1984 | Wartman .............................. 128/90 |
| 4,643,909 | 2/1987 | Kammerer ......................... 128/90 X |

*Primary Examiner*—Richard J. Apley
*Assistant Examiner*—Alan W. Cannon
*Attorney, Agent, or Firm*—Jean B. Mauro

[57] ABSTRACT

New and improved orthopedic/orthotic splint materials are provided which exhibit excellent elasticity, do not easily fingerprint, retain adhesion and have high toughness and flexural strength. The materials employed in the casts of this invention are blends of an aliphatic polyester, such as poly(epsilon-caprolactone), with certain thermoplastic polyurethanes having a hard block segment and a soft block segment, which possess a combination of desirable properties not heretofore found in cast materials.

24 Claims, No Drawings

ORTHOPEDIC/ORTHOTIC SPLINT MATERIALS

FIELD OF THE INVENTION

This invention relates in general to orthopedic/orthotic splint materials. In one aspect, this invention is directed to compositions comprised of aliphatic polyesters, such as poly(epsilon-caprolactone), and certain polyurethanes which render the materials ideally suited for use in the orthopedic applications area. In a further aspect, the present invention is directed to orthopedic/orthotic splint materials that exhibit excellent elasticity, do not easily fingerprint, retain adhesion and have a high toughness and flexural fatigue.

BACKGROUND OF THE INVENTION

Prior to the present invention a variety of thermoplastic and thermosetting polymeric materials were commercially available for use in orthopedic applications. For example, a number of polymeric materials which exhibit thermoplastic properties are known to be useful for the immobilization of fractures. Such materials include, for example, those described in U.S. Pat. No. 2,385,879 which are indicated to be comprised of a copolymer of vinyl acetate and organic phosphate ester plasticizers. Also in U.S. Pat. No. 3,692,023 there is disclosed the use of a poly-caprolactone as a cast material employing porous webs impregnated with the polymer.

Thermoplastic compositions comprised of poly(epsilon-caprolactone), cis-1,4-polyisoprene, and optionally, an ionomer which is a copolymer of ethylene and acrylic or methacrylic acid have been disclosed and claimed in U.S. Pat. No. 4,274,983. Other thermoplastic polyester resins such as those disclosed in U.S. Pat. No. 4,404,333 are indicated to be useful in orthopedic cast material. This patent discloses and claims thermoplastic resins comprised of the reaction product of linear polyester resins and epsilon-caprolactone.

Other orthopedic devices, methods of preparation and use wherein poly(epsilon-caprolactone) is employed as the thermoplastic material are disclosed in the patent literature. For example, in U.S. Pat. No. 4,175,177 there is disclosed crosslinkable copolymers of a lactone, such as epsilon-caprolactone and poly-functional acrylates. It is indicated in the patent that the crosslinked copolymers can be used as plasticizers for vinyl resin compositions or as materials of construction for orthopedic casts and splints. Orthopedic devices are also disclosed in U.S. Pat. No. 4,226,230 which is directed to a method of applying an orthopedic cast which is comprised of a flexible bandage material in the form of a netting and which has been coated with a crosslinkable copolymer of a lactone and an acrylate monomer.

In U.S. Pat. No. 4,238,522 there is disclosed a method for producing a bandage material which can be convertible to an orthopedic cast by first applying an electrically conductive coating to the strands of a netting material and thereafter electrostatically spray coating the strands with a crosslinkable copolymer powder comprised of a lactone and a polyfunctional acrylate monomer. The bandage material is heated to a temperature at which the crosslinked copolymer is soft and self-adherent and is then wrapped around the body portion in overlaying layers to conform to the body contours and then cooled to a rigid state.

An orthopedic cast made from a thermoplastic polyester such as poly(epsilon-caprolactone) which has been subjected to electron radiation is disclosed in U.S. Pat. No. 4,240,415. It is indicated in the patent that the radiation effects crosslinking and desirable modification in the modulus of elasticity. In U.S. Pat. No. 4,286,586 which is a divisional of the above-mentioned U.S. Pat. No. 4,226,230 the invention disclosed and claimed therein is directed to orthopedic casts comprised of a crosslinkable copolymer prepared from a lactone and a polyfunctional acrylate monomer.

A process for producing orthopedic structures is disclosed in U.S. Pat. No. 4,316,457 wherein a bandage material is impregnated or coated with a solvent solution of a polyurethane prepolymer, a bifunctional chain extender and a catalyst. A bifunctional oligomer which can be reacted with diisocyanates for the preparation of polyurethane prepolymers are oligomers of cyclic lactones such as epsilon-caprolactone.

A cold water curable orthopedic cast is described in U.S. Pat. No. 4,427,002. The cast is comprised of a bandage material coated with a cold water curable polyurethane prepolymer. In U.S. Pat. No. 4,483,333 an orthopedic cast material is prepared from a mixture of polyethylene and a thermoplastic polyester having a melting point between 50° C. and 100° C. and a molecular weight of over 5000. Poly(epsilon-caprolactone) and polyethylene are disclosed as the preferred components of the cast system.

Other materials are currently available for use in orthopedic casts and have met with some degree of success as commercially acceptable products. Products containing poly(epsilon-caprolactone) have proven to have significant potential as useful cast materials. Many such products have filler and impact modifiers added to improve basic characteristics and provide a non-tacky product. However, for certain applications, improved elasticity during forming, improved resistance to fingerprinting and improved toughness are desired. For such applications crystalline poly(1,4-isoprene) is widely used although it is characterized by very poor self adhesion. Hence, it was desirable to develop an orthopedic cast material which would inherently possess all of the desired properties and exhibit excellent elasticity, does not easily fingerprint, retains adhesion and has high toughness and flexural strength.

Accordingly, the present invention provides an effective method by which poly(epsilon-caprolactone) can be transformed into a material useful for certain orthopedic applications whereby improved toughness, improved resistance to fingerprinting, and greatly improved elasticity during molding are present. This material also retains excellent self-adhesion whih the polyisoprene products of the prior art do not possess. The combination of properties can only be achieved by a blend of poly(epsilon-caprolactone) and a specific thermoplastic polyurethane is hereinafter described. Other aliphatic polyesters having crystalline melting points of 50°-70° C. may be substituted for the poly(epsilon-caprolactone) in the above blends.

SUMMARY OF THE INVENTION

In its broad aspect, the present invention relates to an orthopedic/orthotic splint material, orthopedic casts prepared from such material and a method for applying such casts to a portion of the human or animal body.

DETAILED DESCRIPTION OF THE INVENTION

As hereinbefore indicated, the present invention is directed to materials suitable for use in the preparation of orthopedic casts and which are blends of an aliphatic polyester, such as poly(epsilon-caprolactone), certain thermoplastic polyurethanes, and optionally additives such as fillers, coloring agents, stabilizers, antimicrobial agents, and the like.

The thermoplastic polymeric materials useful for the preparation of the orthopedic/orthotic splints are comprised of blends of:
(a) from about 90 to about 65 weight percent of an aliphatic polyester having a crystalline melting point of from 50° to 70° C.;
(b) from about 10 to about 35 weight percent of a thermoplastic polyurethane.
and, optionally, up to about 20 weight percent of at least one acceptable additive, added to the blend of the polyester and the polyurethane, the polyurethane being comprised of up to 65 weight percent of a hard block segment formed by the reaction of a diisocyanate and an aliphatic polyol, and at least 35 weight percent of a soft block segment comprised of at least one of a polyether or a polyester.

By the term "hard block" segment as employed throughout the specification and appended claims is meant that portion of the thermoplastic polyurethane component which is crystalline and comprised, in polymerized form, of a diisocyanate as hereinafter indicated, and a short coupling aliphatic diol having from 4 to 6 carbon atoms.

By the term "soft block" segment as employed throughout the specification and appended claims is meant that portion of the thermoplastic polyurethane component which is comprised of, in polymerized form, a diisocyanate, as hereinafter indicated, and:

(a) a polyether of the formula:

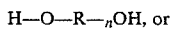

H—O—R—$_n$OH, or (b) a polyester of the formulae:

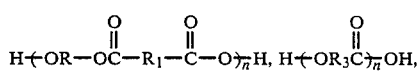

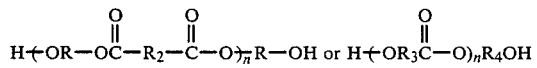

where R, $R_1$, $R_2$, $R_3$ and $R_4$ are aliphatic segments.

As indicated above, the thermoplastic materials which are prepared by the method of the present invention are blends of an aliphatic polyester, such as a poly(epsilon-caprolactone), and a thermoplastic poly-urethane having hard and soft block segments. These materials are conveniently prepared by blending the poly(epsilon-caprolactone) and the polyurethane by conventional blending techniques.

In practice, the aliphatic polyester component is a polymer or copolymer having a melting point of at least about 50° C. Accordingly, this component of the orthopedic splint material can be comprised of a homopolymer, block copolymer, graft copolymer of certain random copolymers containing at least about 50 weight percent of a poly(epsilon-caprolactone) or an appropriate aliphatic polyester with a melting point between 50° and 70° C.

The lactone monomer employed in the preparation of certain of the aliphatic polyester polymeric component can be shown by the following formula:

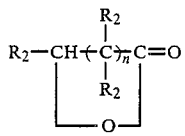

wherein n is an integer having a value of from about 3 to 6, at least n+2 of the $R_2$'s are hydrogen and the remaining $R_2$'s are alkyl of from 1 to 10 carbon atoms.

Illustrative lactone monomers which can be used in the preparation of the poly(lactones) can be mentioned epsilon-caprolactone, zeta-enantholactone, delta-valerolactones, the monoalkyl-delta-valero-lactones, e.g. the monomethyl-, monoethyl-, monohexyl-delta-valerolactones, and the like; the nonalkyl, dialkyl, and trialkyl-epsilon-caprolactones, e.g. the monomethyl-, monoethyl-, monohexyl-, dimethyl-, diethyl-, di-n-propyl-, di-n-hexyl-, trimethyl-, triethyl-, tri-n-propyl-epsilon-caprolactones, and the like.

The lactone polymers employed in the blends of the present invention are prepared from the above lactones by methods known in the art. For use in the blends of the present invention it is preferred that the polylactone have a weight average molecular weight of from about 10,000 to about 90,000 and more preferably from about 20,000 to about 60,000.

Besides poly(epsilon-caprolactone) or lactone polymers in general, other aliphatic polyesters having melting points between 50° and 70° C. include those of the general formula:

where $R_5$ and $R_6$ represent aliphatic units such as

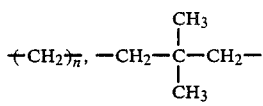

and the like. These aliphatic polyesters are thus derived from the condensation polymerization of diols and carboxylic acids. The diols include ethylene glycol, diethylene glycol, neopentyl glycol, butane diol, hexane diol, and the like. The carboxylic acids could include adipic acid, sebacic acid and the like.

The thermoplastic polyurethane component of the orthopedic splint material of the present invention is comprised of a hard block segment formed by the reaction of a diisocyanate and an aliphatic diol and a soft block segment consisting of a polyether, or a polyester polyol. In practice, the polyurethane component is comprised of at least about 35 weight percent of the soft block segment.

In the preparation of the hard block segment, it is important that the aliphatic diol which reacts with the diisocyanate have a relatively short carbon atom chain. For example, it is preferred that the aliphatic diol have from 4 to 6 carbon atoms in its chain length and thus include diols such as butanediol, pentanediol, hexanediol, and the like.

In general, the polyurethane component of the orthopedic cast material can be prepared by methods known in the art for the preparation of such compositions from diisocyanate and polyol.

The diisocyanates employed in the polyurethane component of the orthopedic splint material of the present invention are those having the formula:

$$OCN-R_3-NCO$$

wherein $R_3$ contains up to 36 carbon atoms and is preferably a divalent, hydrocarbon group containing one or more aliphatic, aromatic or cycloaliphatic groups which can contain fused rings or rings separated by divalent aliphatic groups. Thus, $R_3$ can represent alkylene, cycloalkylene, arylene, arylalkylenearyl, arylalkylene, and the like and wherein such groups can be substituted with lower alkyl groups.

Illustrative diisocyanates which can be employed in the polyurethane component of the blends include, among others, those having the formula:

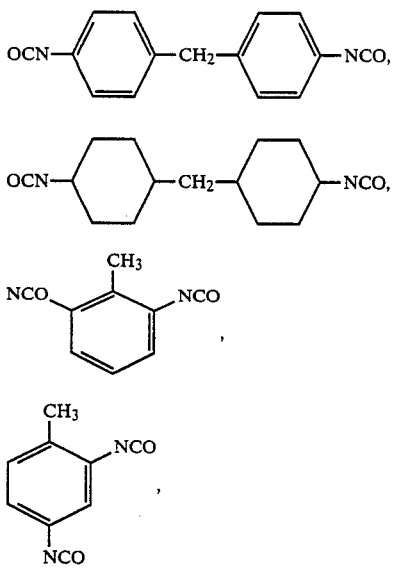

$$OCN+CH_2\overline{)_6}NCO$$

and the like.

The thermoplastic materials of the present invention are prepared by blending the aliphatic polyester [e.g., poly(epsilon-caprolactone)], the polyurethane and additives, if desired, using conventional blending equipment and methods as illustrated in the examples.

In practice it has been found that the preferred materials of the present invention contain about 90 to about 65 weight percent of the poly(epsilon-caprolactone) and from about 10 to about 35 weight percent of the thermoplastic polyurethane component. Particularly preferred are cast materials containing from about 85 to about 75 weight percent of the poly(epsilon-caprolactone) and from about 15 to about 25 weight percent of the polyurethane. As indicated above, the materials may also contain additives and other agents if desired.

The cast or splint materials of the present invention can also contain a wide variety of additives which are customarily employed in such products. For example, fillers and other additives can be employed in the cast materials in amounts up to about 20 weight percent, or more preferably from about 1 to about 15 weight percent. Fillers, such as silica or calcium silicate can be utilized in the cast materials as well as coloring agents, such as titanium dioxide, stabilizers, antioxidants, antimicrobial agents and the like.

The cast materials of the present invention are conveniently prepared using conventional blending and extruding techniques. They can be either extruded into sheet, compression molded into slabs or injection molded into slabs of thicknesses of one sixteenth to one quarter of an inch for use in orthopedic applications.

If desired the cast materials of the present invention can have reinforcing webs, netting or fabrics contain therein. The webs or netting can be sandwiched between thin sheets of the subject material or bonded to the exterior on one side. The addition of fiberglass may also used to give higher stiffness and improved forming characteristics.

In the examples which follow, certain of the components or additives employed in the present invention have been identified by trademark, trade name or an abbreviation for sake of simplicity. These materials are more fully identified below and the manufacture or source of supplier indicated in parentheses after each product.

| Name | Product | Supplier |
|---|---|---|
| P-700 | Poly(epsilon-caprolactone) | Union Carbide |
| Isoplast 101 | Thermoplastic polyurethane based on hard segment: | |

and soft segment: $+CH_2-CH-O\overline{)_{0.23}}+CH_2CH_2O)_{0.11}$ with $CH_3$ substituent

| | | |
|---|---|---|
| Hydrin 100 | Polyepichlorohydrin | B. F. Goodrich |
| Phenoxy PKHH | Polyhydroxyether of Bisphenol A | Union Carbide |
| Attagel 40 | Attapulgus clay | |
| Kraton 3125 | Styrene/butadiene ABA block copolymer | Shell |
| Lexan 101 | Bisphenol A polycarbonate | Gen. Electric |
| DPD-6169 | Ethylene/ethyl acrylate copolymer | Union Carbide |

-continued

| Name | Product | Supplier |
|---|---|---|
| Pellethane 2103-80A | Thermoplastic polyurethane based on MDI, butane diol, and polytetrahydrofuran diol | Upjohn |
| Pellethane 2102-90A 2102-55D | Thermoplastic polyurethanes based on MDI, butane diol, and polyester diol | Upjohn |

The following examples illustrate the present invention.

EXAMPLES A–W

As indicated in the following examples a number of different compositions were experimentally investigated. These were prepared by extrusion blending at proper temperatures and were pelletized in an ice water bath. The pellets were air dried and then injection molded in a 1¼ oz. Newbury reciprocating screw injecting molding machine at the temperatures designated on Tables 1a–1c. The tensile specimens were then evaluated as to the elasticity, fingerprinting, and self-adhesion as set forth in Tables 2a–2c. The elasticity was qualitatively assessed after melting the specimens in a water bath at 65°–70° C. and stretching to about double the grip length and observing the amount of return to original dimensions. No return is rated very poor; complete return is rated as excellent melt elasticity with the other ratings listed as intermediate between the extremes. Fingerprinting resistance was determined by observation after a specimen had been pressed with a thumb to yield obvious deformation. Self-adhesion was determined after the ends of a tensile bar or flexure bar had been pressed together (in the fingerprinting test) and allowed to solidify. The ability to brake the bond was used as the qualitative assessment of self-adhesion. Little to no stress required to break the bond was rated as poor. Inability to break the bond manually was rated as excellent.

Samples of a formulation of 77% P-700/20% Pellethane 2103-80A/3% $TiO_2$ were prepared as above for the poly(epsilon-caprolactone) samples and exhibited excellent elastomeric character, excellent fingerprinting resistance, and good to excellent adhesion when molded at 140°–175° C. Samples were placed in an air circulating oven at 90° C. for 30 minutes on Teflon film. The samples were removable from the film and (after a cooling period) applied to form a hand cast with excellent elastic behavior, no fingerprinting, and excellent adhesion.

The mechanical properties of interest (primarily toughness) were determined on the poly(epsilon-caprolactone)/thermoplastic polyurethane blends and are set forth in Table 3. The notched izod impact strength was determined as per ASTM D-256. The tensile impact strength was determined as per ASTM D-1822. The tensile properties (modulus, strength, elongation) were determined as per ASTM D-638. It is clearly evident from the data set forth in the tables that the notched izod impact strength and tensile impact strength are significantly improved over the unblended poly(epsilon-caprolactone).

It is evident from the number of different modifications of poly(epsilon-caprolactone) that the thermoplastic polyurethane additions offer a unique, desired balance of properties not found with addition of other polymers. This combination offers significant improvements over other modified poly(epsilon-caprolactone) or aliphatic polyesters with a melting point of 50°–70° C. which have been considered or are presently being used in orthopedic/orthotic application areas.

TABLE 1

| | | Injection Molding Conditions | | | | | | |
|---|---|---|---|---|---|---|---|---|
| | | Cylinder Temp (°F.) | | | Mold Temp (°C.) | Screw RPM | Injection Pressure Gauge (psi) | Total Cycle Time (sec) |
| Example | Sample Description | Rear | Mid | Nozzle | | | | |
| control | P-700 Control | 150 | 180 | 160 | 20 | 60 | 500 | 67 |
| A | 90% P-700 10% Isoplast 101 | 150 | 180 | 160 | 20 | 60 | 600 | 52 |
| B | 80% P-700 20% Isoplast 101 | 170 | 190 | 160 | 20 | 60 | 750 | 52 |
| C | 70% P-700 30% Isoplast 101 | 180 | 220 | 180 | 20 | 50 | 800 | 52 |
| D | 90% P-700 10% Lexan 101 | 180 | 180 | 170 | 20 | 70 | 550 | 57 |
| E | 80% P-700 20% Lexan 101 | 180 | 220 | 180 | 20 | 50 | 700 | 57 |
| F | 90% P-700 10% Hydrin 100 | 150 | 180 | 160 | 20 | 70 | 500 | 67 |
| G | 80% P-700 20% Hydrin 100 | 150 | 180 | 170 | 20 | 100 | 550 | 67 |
| H | 80% P-700 20% Phenoxy PKHH | 160 | 180 | 160 | 20 | 80 | 700 | 99 |
| I | 95% P-700 5% Hydrin 100 | 160 | 180 | 160 | 20 | 80 | 500 | 52 |
| J | 85% P-700 5% Hydrin 100 10% Attagel 40 | 160 | 180 | 160 | 20 | 70 | 600 | 52 |
| K | 70% P-700 20% Phenoxy PKHH 10% Attagel 40 | 170 | 190 | 160 | 20 | 40 | 800 | 89 |
| L | 62% P-700 | 170 | 190 | 160 | 20 | 40 | 900 | 94 |

TABLE 1-continued

Injection Molding Conditions

| Example | Sample Description | Cylinder Temp (°F.) Rear | Mid | Nozzle | Mold Temp (°C.) | Screw RPM | Injection Pressure Gauge (psi) | Total Cycle Time (sec) |
|---|---|---|---|---|---|---|---|---|
| | 20% Phenoxy PKHH | | | | | | | |
| | 10% Attagel 40 | | | | | | | |
| | 8% Kraton 3125 | | | | | | | |
| M | 72% P-700 | 190 | 230 | 180 | 20 | 20 | 1000 | 55 |
| | 18% Lexan 101 | | | | | | | |
| | 10% Attagel 40 | | | | | | | |
| N | 75% P-700 | 160 | 180 | 160 | 20 | 70 | 550 | 62 |
| | 25% DPD-6169 EEA | | | | | | | |
| O | 65% P-700 | 180 | 200 | 160 | 20 | 40 | 900 | 55 |
| | 25% Isoplast 101 | | | | | | | |
| | 10% Attagel 40 | | | | | | | |
| P | 80% P-700 | 170 | 200 | 160 | 20 | 60 | 600 | 57 |
| | 20% Pellethane 2103-80A | | | | | | | |
| Q | 80% P-700 | 170 | 200 | 160 | 20 | 60 | 650 | 52 |
| | 20% Pellethane 2102-90A | | | | | | | |
| R | 80% P-700 | 180 | 200 | 160 | 20 | 70 | 600 | 52 |
| | 20% Pellethane 2102-55D | | | | | | | |
| S | 85% P-700 | 160 | 200 | 160 | 20 | 70 | 650 | 53 |
| | 15% Pellethane 2103-80A | | | | | | | |
| T | 80% P-700 | 160 | 200 | 160 | 20 | 50 | 800 | 53 |
| | 20% Pellethane 2103-80A | | | | | | | |
| U | 75% P-700 | 160 | 200 | 160 | 20 | 60 | 855 | 53 |
| | 25% Pellethane 2103-80A | | | | | | | |
| V | 80% P-700 | 190 | 240 | 200 | 20 | 40 | 900 | 53 |
| | 20% Pellethane 2363-55D | | | | | | | |
| W | 70% P-700 | 180 | 200 | 190 | 20 | 70 | 750 | 53 |
| | 18% Pellethane 2103-80A | | | | | | | |
| | 10% Attagel 40 | | | | | | | |

TABLE 2

| Example | Sample Description | Melt Elasticity | Fingerprinting Resistance | Self-Adhesion |
|---|---|---|---|---|
| Control 1 | poly(epsilon-caprolactone) P-700 | very poor | very poor | excellent |
| Control 2 (Orthoplast) | trans 1,4-polyisoprene | excellent | excellent | poor |
| A | 90% P-700 | poor | poor | excellent |
| | 10% Isoplast 101 | | | |
| B | 80% P-700 | fair | fair | excellent |
| | 20% Isoplast 101 | | | |
| C | 70% P-700 | good | fair | excellent |
| | 30% Isoplast 101 | | | |
| D | 90% P-700 | fair | poor | excellent |
| | 10% Lexan 101 | | | |
| E | 80% P-700 | good | fair to good | excellent |
| | 20% Lexan 101 | | | |
| F | 90% P-700 | shrinks | fair to good | excellent |
| | 10% Hydrin 100 | | | |
| G | 80% P-700 | shrinks | good to excellent | excellent |
| | 20% Hydrin 100 | | | |
| H | 80% P-700 | poor | poor | excellent |
| | 20% Phenoxy PKHH | | | |
| I | 95% P-700 | shrinks | fair to poor | excellent |
| | 5% Hydrin 100 | | | |
| J | 85% P-700 | fair | fair | excellent |
| | 5% Hydrin 100 | | | |
| | 10% Attagel 40 | | | |
| K | 70% P-700 | good | fair | excellent |
| | 20% Phenoxy PKHH | | | |
| | 10% Attagel 40 | | | |
| L | 62% P-700 | good | fair | excellent |
| | 20% Phenoxy PKHH | | | |
| | 10% Attagel 40 | | | |
| | 8% Kraton 3125 | | | |
| M | 72% P-700 | good | fair | excellent |
| | 18% Lexan 101 | | | |

TABLE 2-continued

| Example | Sample Description | Melt Elasticity | Fingerprinting Resistance | Self-Adhesion |
|---|---|---|---|---|
| N | 10% Attagel 40<br>75% P-700<br>25% DPD-6169 EEA | good | good | excellent |
| O | 65% P-700<br>25% Isoplast 101<br>10% Attagel 40 | good | fair | excellent |
| | (Samples Compression Molded at 140° C. to 175° C.) | | | |
| P | 80% P-700<br>20% Pellethane 2103-80A | excellent | excellent | excellent |
| Q | 80% P-700<br>20% Pellethane 2102-90A | good to excellent | good to excellent | excellent |
| R | 80% P-700<br>20% Pellethane 2102-55D | good | good | excellent |
| S | 85% P-700<br>15% Pellethane 2103-80A | excellent | excellent | excellent |
| T | 80% P-700<br>20% Pellethane 2103-80A | excellent | excellent | excellent |
| U | 75% P-700<br>25% Pellethane 2103-80A | excellent | excellent | good |
| V | 80% P-700<br>20% Pellethane 2363-55D | excellent | excellent | excellent |
| W | 70% P-700<br>18% Pellethane 2103-80A<br>10% Attagel 40<br>2% TiO$_2$ | excellent | excellent | excellent |

TABLE 3

| Example | Sample Description | Tensile Modulus (psi) | Tensile Strength (psi) | % Elongation | Tensile Impact Strength ft-lbs/in | Notched Izod Impact Strength ft-lbs/in of notch |
|---|---|---|---|---|---|---|
| Control | Poly(epsilon-caprolactone) P-700 | 59,000 | >2,550* | >423* | 51 | 3.1 |
| P | 80% P-700<br>20% Pellethane 2103-80A | 43,600 | >2,200* | >425* | 82 | 10.5 |
| Q | 80% P-700<br>20% Pellethane 2102-90A | 51,700 | >2,850* | >400* | 79 | 10.2 |
| R | 80% P-700<br>20% Pellethane 2102-55D | 53,700 | >2,860* | >390* | 72 | 3.0 |
| S | 85% P-700<br>15% Pellethane 2103-80A | 45,300 | >2,570* | >367* | 66 | 13.5 |
| T | 80% P-700<br>20% Pellenthane 2103-80A | 44,500 | >2,660* | >338* | 64 | 14.3 |
| U | 75% P-700<br>25% Pellethane 2103-80A | 40,500 | >2,800* | >323* | 71 | 13.2 |
| V | 80% P-700<br>20% Pellethane 2363-55D | 51,900 | >3,590* | >300* | 59 | 15.2 |
| W | 70% P-700<br>18% Pellethane 2103-80A<br>10% Attagel 40<br>2% TiO$_2$ | 54,600 | >2,060* | >422* | 25 | 8.4 |

*Samples did not break during tensile testing.

Although the invention has been illustrated by the preceding examples it is not to be construed as being limited to the materials employed therein, but rather, the invention is directed to the generic area as hereinbefore disclosed. Various modifications and embodiments thereof can be made without departing from the spirit and scope thereof.

What is claimed is:

1. A thermoplastic polymeric material useful in the preparation of orthopedic/orthotic splints comprised of a blend of:
   (a) from about 90 to about 65 weight percent of an aliphatic polyester having a crystalline melting point of from 50°–70° C.,
   (b) from about 10 to about 35 weight percent of a thermoplastic polyurethane,
and optionally, up to about 20 weight percent of at least one orthopedically acceptable additive, added to said blend of said aliphatic polyester and said polyurethane, said polyurethane comprised of up to 65 weight percent of a hard block segment formed by the reaction of a diisocyanate and an aliphatic polyol, and at least 35 weight percent of a soft block segment comprised of at least one of a polyether or a polyester.

2. The thermoplastic polymeric material of claim 1 wherein the aliphatic polyester has a weight average molecular weight of from about 10,000 to about 90,000.

3. The thermoplastic polymeric material of claim 1 wherein the aliphatic polyester has a weight average molecular weight of from about 20,000 to about 60,000.

4. The thermoplastic polymeric material of claim 1 wherein the aliphatic polyester is poly(epsilon-caprolactone).

5. The thermoplastic polymeric material of claim 1 wherein the thermoplastic polyurethane is based on a methylene bis(para-isocyanatophenyl)butane diol hard block segment and a poly(tetrahydrofuran) soft block segment.

6. The thermoplastic polymeric material of claim 1 wherein the thermoplastic polyurethane is based on a methylene bis(para-isocyanatophenyl)butane diol hard block segment and an aliphatic polyester soft block segment.

7. The thermoplastic polymeric material of claim 1 which contains an additive.

8. The thermoplastic polymeric material of claim 7 wherein the additive is a silica filler.

9. The thermoplastic polymeric material of claim 7 wherein the additive is attapulgus clay.

10. The thermoplastic polymeric material of claim 7 wherein the additive is titanium dioxide.

11. An orthopedic/orthotic cast configured to conform to at least one portion of the animal or human anatomy so as to immobilize said portion, said cast comprised of a blend of:
 (a) from about 90 to about 65 weight percent of an aliphatic polyester having a crystalline melting point of from 50°-70° C.,
 (b) from about 10 to about 35 weight percent of a thermoplastic polyurethane,
and optionally, up to about 20 weight percent of at least one orthopedically acceptable additive, added to said blend of said aliphatic polyester and said polyurethane, said polyurethane comprised of up to 65 weight percent of a hard block segment formed by the reaction of a diisocyanate and an aliphatic polyol, and at least 35 weight percent of a soft block segment comprised of at least one of a polyether or a polyester.

12. The orthopedic/orthotic cast of claim 11 wherein the aliphatic polyester is poly(epsilon-caprolactone).

13. The orthopedic/orthotic cast of claim 11 wherein the aliphatic polyester has a weight average molecular weight of from about 10,000 to about 90,000.

14. The orthopedic/orthotic cast of claim 11 wherein the poly(epsilon-caprolactone) has a weight average molecular weight of from about 20,000 to about 60,000.

15. The orthopedic/orthotic cast of claim 11 wherein the thermoplastic polyurethane is based on a methylene bis(para-isocyanatophenyl)-butane diol hard block segment and a poly(tetrahydrofuran) soft block segment.

16. The orthopedic/orthotic cast of claim 11 wherein the thermoplastic polyurethane is based on a methylene bis(para-isocyanatophenyl)-butane diol hard block segment and an aliphatic polyester soft block segment.

17. The orthopedic/orthotic cast of claim 11 which contains an additive.

18. The orthopedic/orthotic cast of claim 17 wherein the additive is a silica filler.

19. The orthopedic/orthotic cast of claim 17 wherein the additive is attapulgus clay.

20. The orthopedic/orthotic cast of claim 17 wherein the additive is titanium dioxide.

21. The orthopedic/orthotic cast of claim 11 which contains embedded therein a reinforcing structure.

22. The orthopedic/orthotic cast of claim 21 wherein the reinforcing structure is a web.

23. The orthopedic/orthotic case of claim 21 wherein the reinforcing structure is a netting.

24. The orthopedic/orthotic cast of claim 21 wherein the reinforcing structure is a fabric.

* * * * *

UNITED STATES PATENT AND TRADEMARK OFFICE
CERTIFICATE OF CORRECTION

PATENT NO. : 4,784,123
DATED : November 15, 1988
INVENTOR(S) : Lloyd M. Robeson

It is certified that error appears in the above-identified patent and that said Letters Patent is hereby corrected as shown below:

Column 3, line 66, the word "of" should be -- or --.

Column 11, line 54, the word "generatic" should be -- generic --.

Signed and Sealed this

Seventeenth Day of October, 1989

Attest:

DONALD J. QUIGG

Attesting Officer

Commissioner of Patents and Trademarks